United States Patent
Steinbrenner et al.

(10) Patent No.: US 7,408,083 B2
(45) Date of Patent: Aug. 5, 2008

(54) METHOD FOR THE PRODUCTION OF DIAMINODIARYLMETHANES

(75) Inventors: Ulrich Steinbrenner, Neustadt (DE); Eckhard Stroefer, Mannheim (DE); Martin Sohn, Lohra (DE); Veronika Quaschning, Mannheim (DE); Helmut Moehwald, Annweiler (DE); Kai Thiele, Schwarzheide (DE); Filip Deberdt, Muizen (BE); Jan D. Jacobs, Baton Rouge, LA (US); Rolf Pinkos, Bad Durkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 20 days.

(21) Appl. No.: 10/564,059

(22) PCT Filed: Jun. 25, 2004

(86) PCT No.: PCT/EP2004/006912

§ 371 (c)(1),
(2), (4) Date: Aug. 8, 2006

(87) PCT Pub. No.: WO2005/007613

PCT Pub. Date: Jan. 27, 2005

(65) Prior Publication Data

US 2007/0010692 A1    Jan. 11, 2007

(30) Foreign Application Priority Data

Jul. 11, 2003  (DE) ................ 103 31 772

(51) Int. Cl.
*C07C 209/78*   (2006.01)
(52) U.S. Cl. .................. 564/331; 564/332; 564/333
(58) Field of Classification Search ............... 564/333
See application file for complete search history.

(56) References Cited

U.S. PATENT DOCUMENTS 6,433,219 B1 *  8/2002  Strofer et al. ............... 560/347

FOREIGN PATENT DOCUMENTS

| DE | 196 13 554 | 11/1997 |
|---|---|---|
| DE | 100 27 778 | 12/2001 |
| DE | 101 16 316 | 10/2002 |
| EP | 0 109 931 | 5/1984 |
| EP | 0 329 075 | 8/1989 |
| EP | 0 462 697 | 12/1991 |
| EP | 1 063 221 | 12/2000 |
| EP | 1 167 343 | 1/2002 |
| WO | 94/23099 | 10/1994 |
| WO | 99/40059 | 8/1999 |
| WO | 99/57161 | 11/1999 |
| WO | 01/58847 | 8/2001 |

OTHER PUBLICATIONS

Mueller. "Methoden der Organischen Chemie, Band I/1", George Thieme Verlag, pp. 557-558, XP002306225 1958.
Schauerte et al. "Isocyanate", Kunststoffhandbuch, vol. 7, Polyurethane, pp. 76-86 1993.

* cited by examiner

*Primary Examiner*—Brian J Davis
(74) *Attorney, Agent, or Firm*—Oblon, Spivak, McClelland, Maier & Neustadt, P.C.

(57) ABSTRACT

A process is described for preparing diaminodiarylmethanes comprising the steps
a) reacting an aromatic amine with a methylene-donating agent in the presence of homogeneous acid catalysts,
b) removing the homogeneous acid catalyst from the reaction product,
c) working up and purifying the reaction product,
which comprises removing the homogeneous acid catalyst from the reaction mixture by adsorption to a solid adsorbent.

20 Claims, No Drawings

METHOD FOR THE PRODUCTION OF DIAMINODIARYLMETHANES

The present invention relates to a process for preparing diaminodiarylmethanes.

Diaminodiarylmethanes are usually prepared by condensing the corresponding amines with formaldehyde or its storage-stable forms. These storage-stable forms are, for example, commercially conventional aqueous formalin solutions, paraformaldehyde, trioxane or high-concentration formalin solutions, as are described in EP 1 167 343, EP 1 063 221 or DE 100 27 778.

To ensure complete conversion of compounds formed as intermediates, for example aminobenzylanilines, the use of an acid catalyst is necessary. The resultant crude diaminodiarylmethane consists of a mixture of two-ring and three-ring compounds and higher oligomers. The compounds are usually present as ortho and para isomers.

One example of diaminodiarylmethanes is 3,3'-dimethyl-4,4'-diaminodiphenylmethane, which is also called toluidine base. This compound can be used as precursor for nuclear-hydrogenated special amines which act, especially, as epoxide resin curers for producing glass-clear polyamide. A further possible use is reacting the toluidine base with phosgene to give the corresponding special isocyanate. A process for preparing this product by the semibatch process is described in DE 101 16 316.

Another industrially important diaminodiarylmethane is diaminodiphenylmethane, also called methylenedianiline (MDA). This compound predominantly acts as precursor for preparing the corresponding isocyanate diphenylmethane diisocyanate (MDI), which is chiefly used for preparing polyurethanes. MDA can be prepared continuously or semicontinuously and has been described many times in the literature. A semibatch process for preparing this product is described in U.S. Pat. No. 6,433,219.

In said compounds it is desirable to achieve a content of binuclear compounds in the reaction product which is as high as possible. In the case of MDI the binuclear product, and in particular the 4,4'-isomer, is of great industrial importance. In the case of toluidine base, there is actually only one significant market for the 4,4' two-ring compound.

These two-ring compounds, possibly also after nuclear hydrogenation has been carried out, may be synthesized by phosgenation in a gas-phase process, as described, for example, in EP 570 799. Higher oligomers are not synthesized in the phosgenation in a gas-phase process, since they cannot be vaporized without decomposition. Manufacturers of polyurethanes are increasingly preferentially using two-ring compounds since these have a lower viscosity than higher oligomers. In addition, in their production, not only MDI, but also MDA, can be purified by distillation. The color values of the polyurethanes prepared from binuclear-MDI are generally lower than the color values of the polyurethanes which are produced from higher oligomers, also termed crude MDI. Prepolymers can also be prepared from the binuclear compounds by reaction with polyols, which prepolymers are suitable for many fields of use in the production of polyurethanes.

There is thus a great requirement for binuclear compounds, and particularly the paraisomers among these. These should be produced with high selectivity toward just these compounds in the amine condensation stage. An increased content of acid catalyst in the reaction mixture in the condensation stage can shift the reaction toward an increased content of binuclear product and, here, particularly the 4,4' two-ring compound. A further advantage of an increased use of acid is the increase in reaction rate. Customarily the acid is neutralized with bases after the condensation and the resultant salts are removed. This leads to a high consumption of acid and neutralizing agent and also to an unwanted salt load.

The acid can also be removed after the condensation by extraction from the condensate with water. Here, however, the space-time yield decreases and the circulated streams increase.

WO 01/58847 describes a process for preparing MDA having a high binuclear content in which a dried condensate of aniline and the form of formaldehyde administered is reacted at a molar ratio of from 1.7 to 100 in the presence of solid inorganic acid catalysts. This is said to avoid the disadvantages in the process procedure using mineral acids, in particular the increased consumption of acid which must then be laboriously removed from the reaction mixture.

However, the process described there also has disadvantages. These are, in particular, the inadequate service life of the catalyst due to deactivation owing to coating formation with oligomers, the titration of the acid groups of the catalyst with secondary amines present in the aniline or formed during the reaction, such as N-methylamines, and also the high costs of the catalyst and down times due to change and regeneration of the catalyst, which must be made up for by a corresponding service life of the catalyst.

It is an object of the present invention, therefore, to develop a process for preparing diaminodiarylmethanes having a high binuclear content, in which the acid is used as homogeneous catalyst without the necessity of a complex removal of the acid and the associated disadvantages, such as the high acid consumption and the elevated salt load in the wastewater.

We have found that this object is achieved, surprisingly, by the acid, after the reaction, being wholly or partially adsorbed to a basic ion exchanger.

The invention thus relates to a process for preparing diaminodiarylmethanes comprising the steps a) reacting an aromatic amine with a methylene-donating agent in the presence of homogeneous acid catalysts, b) removing the homogeneous acid catalyst from the reaction product, and optionally c) working up and purifying the reaction product, which comprises removing the homogeneous acid catalyst from the reaction mixture by adsorption to a solid adsorbent.

If appropriate, it is possible to subject the reaction mixture, after the adsorption of the homogeneous acid catalyst, to a further re-neutralization using customary basic neutralizing agents, such as amines or alkali metal hydroxides, to remove the last traces of the acid. The resultant salt load here, however, is substantially lower than when the entire amount of the homogeneous acid catalyst is neutralized using basic neutralizing agents. For certain fields of use of the diaminodiarylmethanes, for example the preparation of polyisocyanates, a residual acid content can also remain in the product.

The adsorbent is preferably a basic ion exchanger prepared on the basis of higher oligomers of diphenylmethanediamine or on the basis of an inorganic or organic support material having active basic centers.

The base strength of these ion exchangers preferably differs by +/−1.0 $pK_B$ units, in particular +/−0.5 $pK_B$ units, from that of the aromatic amine in aqueous solution. The base strength of the amine and of the ion exchanger can be determined by means of acid-base titration.

In a preferred embodiment, >80%, preferably >90%, in particular >95%, of the active basic centers of the adsorbent consist of aromatic or aliphatic amines, in particular aniline and toluidine units.

The ion exchanger used as adsorbent can consist either of active centers applied to a support or of a polymer or copolymer containing these active centers. Suitable supports are polymers, customary inorganic supports, activated carbons, or metals. The active components can be bound to these supports via van der Walls bonds, but preferably via ionic bonds, and particularly preferably via covalent bonds, for example by using C—C or O—Si—C bridges.

In one embodiment of the inventive process, the adsorbents used are higher oligomers of diphenylmethanediamines which contain the necessary active centers. These oligomers can be prepared, for example, by condensing aromatic amines with a methylene-donating agent, in particular in the presence of homogeneous acid catalysts, under those conditions favoring the formation of high-molecular-weight reaction products. Products of this type can also be prepared by crosslinking with one another in a suitable manner condensation products of aromatic amines with a methylene-donating agent which have a relatively low molecular weight, in particular those having 2 to 5 aromatic nuclei in the molecule. It is essential that the oligomers are solid under the conditions of the adsorption. Very particular preference is given to the use of higher condensation products of aniline or toluidine and carbonyl compounds, preferably ketones and/or aldehydes, in particular formaldehyde.

In a further embodiment of the inventive process, the adsorbents used are ion exchangers of a support having active centers situated thereon. The active centers can be a constituent of the support or be applied to the support subsequently. The supports must be suitable in the last mentioned embodiment for applying the active centers.

Suitable polymeric supports are, for example, polyethylene, polypropylene, polystyrene, polyamides, polyesters, polyethers, polysulfones, polyethersulfones, polyketones, polyurethanes, polytetrafluoroethylene, polyvinylidene fluoride, polyaniline, polypyrrole and polythiophene.

Suitable polymeric supports are also copolymers obtainable by polymerizing at least one condensation product of at least one compound which is able to react with a carboxylic acid or a derivative of a carboxylic acid, at least one mole per mole of this compound of a carboxylic acid which has at least one functional group which can be polymerized by a free-radical mechanism, or a derivative thereof, and, optionally, a further compound having a mean molecular weight (number average) of at least 5000 having polyether segments in the main chain, as are described, for example, in WO 99/57161, pages 29 to 30.

A further group of polymeric supports are crosslinkable polymers. These are obtained by free-radical polymerization, poly addition or polycondensation of monomer building blocks which, in addition to the groups via which the polymer is built up, also have one or more further reactive groups so that the crosslinkable polymers are already formed during the production of the polymer. Typical examples thereof are polyesters which are prepared using unsaturated carboxylic acids, for example (meth)acrylic acid. Polymers of this type are described in WO 99/57161, pages 22 to 28, for example.

Suitable inorganic supports are, for example, oxides, such as silica, alumina, magnesium oxide or titanium dioxide, mixed oxides, for example the elements silicon, calcium, aluminum, magnesium, titanium, silicates such as double-strand, single-strand, sheet and framework silicates, such as talcum, porphyrite, muscovite, zeolites, feldspars, wollastonite, mica, carbonates and/or phosphates.

The inventively used ion exchanger is preferably used in the form of granules or extrudate. The ratio of surface area and volume of the shaped bodies is $>0.2$ mm$^{-1}$, preferably $>0.5$ mm$^{-1}$, particularly preferably $>1$ mm$^{-1}$. The particle volume is $<300$ mm$^3$, preferably $<100$ mm$^3$, particularly preferably $<50$ mm$^3$. The fines content, that is particles of $<0.1$ mm$^3$, is $<10\%$ by weight, preferably $<5\%$ by weight.

The shaped bodies of the ion exchanger are preferably introduced in the basic state into a fixed bed. The ion exchanger can be operated in a two- or three-phase cycle of adsorption, optional rinsing, and regeneration.

The respective flow rates here are usually less than 30 bed volumes, preferably $<10$ bed volumes, particularly preferably $<5$ bed volumes, per hour.

The ion exchanger has a porosity, or in the reaction mixture has a swelling behavior, such that, in operation for pure aniline diffusing in the shaped body at 20° C. this results in an apparent diffusion coefficient $>10^{-8}$ cm$^2$/s, preferably $>5*10^{-7}$ cm$^2$/s. The apparent diffusion coefficient is defined here as $$D = \frac{I}{d\vec{A} \cdot \vec{\nabla} c}$$

where the measurable stream I [mol/s] through a small area element dA and the concentration of amine c [mol/l] is based on the free liquid phase, that is to say without taking into account the volume which is taken up by the ion exchanger. D can readily be determined by methods such as Pulsed Field-Gradient NMR or exchange experiments.

As described, the reaction mixture from the reaction of the aromatic amines with the methylene-donating agent is worked up by removing the acid catalyst by an adsorbent.

In the first step, reaction mixture containing the acid anion to be recovered is passed over the adsorbent. The adsorption phase is ended as soon as the concentration of the acid anion in the effluent solution is $>50\%$, preferably $>10\%$, particularly preferably $>1\%$, of the influent solution. The residual acid content which can remain in the reaction mixture depends on the intended field of use of the diaminodiarylmethane. The apparatus, in particular the fixed bed, in which the adsorbent is situated, can be designed accordingly. It is also possible to arrange a plurality of such apparatus in series, or to connect a plurality of such apparatus in parallel, to switch the product stream, as required, from one apparatus to the other.

When the adsorbent has reached its capacity, it is regenerated.

Before the regeneration, a wash phase can be carried out. In this case the product remaining in the ion-exchange bed is washed out in counter current with a base, in particular an amine, preferably the amine used as starting material, into the product stream loaded with acid. As a result, diaminodiarylmethane and other constituents of the product stream which have settled on the surface of the adsorbent and thus impair its efficiency are also removed.

The adsorbent is regenerated, in particular, by treating it with a base, in particular an amine, preferably in counter current. Preferably the feed product of the inventive process is used for the regeneration, that is to say in the preparation of MDA, aniline, and in the preparation of toluidine base, toluidine. The acid-loaded amine can, if appropriate in a mixture with the product stream originating in the washing, be fed back from the regeneration directly to the inventive process as feed product, in which case, if appropriate by adding further acid, or removing amine, preferably by distillation, the ratio of acid to amine required for the process can be set. By this arrangement of the process the great majority of the acid can be recirculated, which leads to savings in acid and neutralizing agent and also to reduction in the amount of waste products.

The regeneration is terminated when the concentration of the acid anion in the effluent solution is <20%, preferably <10%, particularly preferably <1%, of the concentration of the acid anions present in the effluent solution at the start of the regeneration process.

Regeneration solutions and, if appropriate, wash solutions are reconditioned to a composition suitable for the upstream formaldehyde condensation by distillation and/or fortification with amine and/or acid.

The diaminodiarylmethanes are prepared, as described above, by reacting an aromatic amine with a methylene-donating agent in the presence of homogeneous acid catalysts. Processes of this type are generally known, and are described, for example, in Kunststoffhandbuch [Plastics handbook], Volume 7, Polyurethanes, Carl Hanser Verlag Munich Vienna, $3^{rd}$ edition, 1993, pages 76 to 86, and also in a great number of patent applications, for example WO 99/40059.

The methylene-donating agent is preferably formaldehyde or a compound releasing formaldehyde. In particular, the formaldehyde is used as aqueous formalin solution, alcoholic formalin solution, hemiacetal, methyleneimine of a primary amine or N,N'-methylenediamine of a primary or secondary amine and also paraformaldehyde. Preference is given to aqueous formalin solution and methyleneimine or di-, oligo- or polymeric N,N'-methylenediamines of the starting products of the inventive process, that is to say in the preparation of MDA, aniline, and in the preparation of toluidine base, toluidine.

Homogeneous acid catalysts used are, in particular, mineral acids, and, here, preferably hydrochloric acid.

The inventive process can be carried out continuously, semicontinuously or batchwise, preferably continuously or semicontinuously.

In the continuous procedure, the reactants are metered into a reactor in the desired ratio to one another and, from this reactor, an amount of reaction product equal to the influent stream is taken off. Reactors used are, for example, tubular reactors. In the continuous or semicontinuous procedure, the reactants are metered into a batch reactor preferably provided with an agitator and/or a pumped circulation, from which the completely reacted reaction product is taken off and fed to the workup.

The inventive process is preferably carried out at a molar ratio of aniline to formaldehyde greater than 2. The molar ratio of acid to aniline is preferably greater than 0.05. At these ratios, there is an intensified formation of the respective binuclear products in the reaction mixture.

The reaction is preferably carried out at a temperature in the range from 0 to 200° C., preferably from 20 to 150° C., and in particular from 40 to 120° C. It has been found that the proportion of the 2,2'- and 2,4'-isomers in the reaction product increases with the increase in temperature.

The pressure in the reaction is from 0.1 to 50 bar absolute, preferably from 1 to 10 bar absolute.

When the reaction is carried out batchwise and semicontinuously, after complete metering of the starting materials, the reaction mixture may be subjected to what is termed aging. For this the reaction mixture is left in the reactor or is transferred to another, preferably stirred, reactor. In the course of this the temperature of the reaction mixture is preferably above 75° C., in particular in a range from 110 to 150° C.

The preparation of the condensation product is followed by the inventive workup described in more detail above.

Remaining traces of acid in the reaction product can be neutralized with alkali metal hydroxide solution. The product mixtures are worked up further as in customary processes for preparing condensation products of this type, for example by phase separation, distillation and/or chromatographic separation methods.

The diaminodiarylmethanes prepared and worked up in this manner can be processed further by the customary and known processes.

The MDA can be processed further, for example, by reaction with alkylene oxides to form polyether alcohols.

Principally, the MDA is reacted with phosgene to form MDI. Processes of this type are generally known and have been described many times, for example in Kunststoffhandbuch [Plastics handbook], Volume 7, Polyurethanes, Carl Hanser Verlag Munich Vienna, $3^{rd}$ edition, 1993, pages 76-86, and also in a great number of patent applications, for example WO 99/40059 or WO 99/54289.

For this, customarily the MDA, and, if appropriate, the phosgene, are dissolved in an inert solvent and brought to reaction.

Said process can be carried out in conventional reactors, for example stirred tanks, stirred tank cascades, columns and/or tubular reactors at known temperatures of, for example, from 50 to 150° C., preferably from 70 to 120° C., particularly preferably from 70 to 100° C., and at a pressure of from 0.5 to 10 bar, preferably from 0.8 to 5 bar, particularly preferably from 0.8 to 1.5 bar, in one or more stages.

For example, the phosgenation can be carried out by a two-stage reaction in the presence of at least one inert organic solvent, in which case the first stage of the phosgenation is carried out in a static mixer and the second stage of the phosgenation in a retention apparatus.

The crude MDI prepared by the phosgenation can be purified by conventional processes, for example distillation. Preferably, in a first purification operation, phosgene and, if appropriate, solvent, can be removed from the phosgenation reaction mixture, that is to say the crude MDI, preferably substantially, particularly preferably completely.

Preferably, desired monomeric MDI, for example 2,2'-, 2,4'- and/or 4,4'-MDI and/or mixtures containing at least two of these isomers can then be separated off by a suitable process, preferably by distillation, for example at pressures of from 2 to 50 mbar, preferably 2 to 20 mbar, and temperatures of from 150 to 250° C., preferably from 180 to 230° C., and/or preferably by crystallization, for example fractional crystallization.

In a particular embodiment of the process for preparing MDI, the binuclear product can be separated off from the crude MDA and can be reacted to form binuclear MDI by means of gas-phase phosgenation, for example as described in EP 570 799.

The MDI thus prepared can be reacted, in particular, with compounds having at least two active hydrogen atoms to form polyurethanes.

By means of the inventive process it is possible, in the preparation of diaminodiarylmethanes, to reduce significantly the required amount of acid. As a result the production costs can be decreased and the amount of salt formed as waste product can be reduced.

We claim:
1. A process for preparing diaminodiarylmethanes comprising the steps
   a) reacting an aromatic amine with a methylene-donating agent in the presence of homogeneous acid catalysts, b) removing the homogeneous acid catalyst from the reaction product, c) working up and purifying the reaction product, which comprises removing the homogeneous acid catalyst from the reaction mixture by adsorption to a solid adsorbent and the absorbent is regenerated with the amine which is used as the feed product of the process.

2. The process according to claim 1, wherein the adsorbent is a basic ion exchanger prepared on the basis of higher oligomers of diphenylmethanediamine or on the basis of functionalized support material.

3. The process according to claim 1, wherein the base strength of the adsorbent differs by +/−1.0 p$K_B$ units from that of the aromatic amine in aqueous solution.

4. The process according to claim 1, wherein the base strength of the adsorbent differs by +/−0.5 P$K_B$ units from that of the aromatic amine in aqueous solution.

5. The process according to claim 1, further comprising desorbing said acid homogeneous catalyst with said aromatic amine and recirculated to the reaction.

6. The process according to claim 1, wherein the reaction in step a) is carried out semicontinuously.

7. The process according to claim 1, wherein the aromatic amine is at least one selected from the group consisting of aniline and alkylanilines having from 1 to 3 carbons in the alkyl chain.

8. The process according to claim 1, wherein the aromatic amine is at least one selected from the group consisting of aniline and o-toluidine.

9. The process according to claim 1, wherein the methylene-donating agent is formaldehyde.

10. The process according to claim 1, wherein said methylene-donating agent is used as aqueous formalin solution or paraformaldehyde.

11. The process according to claim 1, wherein said aromatic amine is aniline and said methylene-donating agent is formaldehyde and wherein a molar ratio of aniline to formaldehyde is greater than 2.

12. The process according to claim 1, wherein said aromatic amine is aniline and wherein a molar ratio of acid to aniline is greater than 0.05.

13. The process according to claim 1, wherein mineral acids are used as homogeneous acid catalysts.

14. The process according to claim 1, further comprising, after step b), neutralizing said acid catalyst with an alkali metal hydroxide solution.

15. The process according to claim 1, wherein working up comprises at least one of phase separation, distillation and chromatographic separation.

16. The process according to claim 1, further comprising reacting said diaminodiarylmethane with an alkylene oxide to form a polyether alcohol.

17. The process according to claim 1, further comprising reacting said diaminodiarylmethane with phosgene to form a diarylmethane diisocyanate.

18. The process according to claim 17, further comprising reacting said diarylmethane diisocyanate with a compound having at least two active hydrogen atoms to form a polyurethane.

19. The process according to claim 1, wherein step b) is conducted at a flow rate of less than 30 bed volumes per hour.

20. The process according to claim 1, wherein said solid absorber has an apparent diffusion coefficient of $>10^{-8}$ cm$^2$/s.

* * * * *